United States Patent [19]

Larrabee

[11] 4,092,546
[45] May 30, 1978

[54] PROTECTIVE SHIELDING ASSEMBLY FOR USE IN LOADING A HYPODERMIC SYRINGE WITH RADIOACTIVE MATERIAL

[75] Inventor: Edward Whittum Larrabee, Bronxville, N.Y.

[73] Assignee: Union Carbide Corporation, New York, N.Y.

[21] Appl. No.: 690,831

[22] Filed: Jun. 8, 1976

Related U.S. Application Data

[63] Continuation-in-part of Ser. No. 587,179, Jun. 16, 1975, Pat. No. 3,993,063.

[51] Int. Cl.² .......................................... G21C 11/00
[52] U.S. Cl. .............................. 250/515; 250/432 R; 250/506
[58] Field of Search ................ 250/432 R, 515, 519, 250/432 PD, 506; 128/1.1, 272, 214.2

[56] References Cited

U.S. PATENT DOCUMENTS

| | | | |
|---|---|---|---|
| 3,336,924 | 8/1967 | Sarnoff et al. | 128/272 |
| 3,628,523 | 12/1971 | Pirtle et al. | 128/2 |
| 3,673,411 | 6/1972 | Glasser | 250/505 |
| 3,820,541 | 6/1974 | Langan | 128/215 |
| 3,973,554 | 8/1976 | Tipton | 250/506 |
| 3,977,555 | 8/1976 | Larson | 128/272 |

*Primary Examiner*—Harold A. Dixon
*Attorney, Agent, or Firm*—James C. Arvantes

[57] ABSTRACT

The disclosure of this application is directed to a protective shielding assembly suitable for use in the loading of a hypodermic syringe with radioactive material. The protective shielding device receives and securely holds, at one end, a vial which contains the material to be loaded and at its opposite end a hypodermic syringe with the needle of the syringe approximately centered with respect to the septum of the vial. Penetration of the septum of the vial is effected by moving the slidable members of the protective shielding assembly toward the vial which in turn moves the hypodermic syringe causing the needle of the hypodermic syringe to rupture the vial septum and enter the vial.

6 Claims, 4 Drawing Figures

PROTECTIVE SHIELDING ASSEMBLY FOR USE IN LOADING A HYPODERMIC SYRINGE WITH RADIOACTIVE MATERIAL

RELATED APPLICATIONS

This application is a continuation-in-part application of U.S. patent application Ser. No. 587,179, filed June 16, 1975 now U.S. Pat. No. 3,993,063.

This invention relates to an assembly suitable for use in the loading of a hypodermic syringe, especially the loading of a hypodermic syringe with radioactive material or a solution thereof. More particularly, this invention relates to a protective shielding assembly, suitable for use in the loading of a hypodermic syringe with radioactive material, which can be readily engaged to and disengaged from a dose vial and a hypodermic syringe, provides an accurate alignment of the needle of the hypodermic syringe with the center of the vial septum to be penetrated, controls the degree of penetration of the vial by the needle of the hypodermic syringe and protects the person who is loading the syringe from exposure to radiation emitted by the radioactive material.

Currently, radioactive material is widely used in the diagnosis and treatment of various diseases and body disorders. The radioactive material is generally injected into the body of a patient by means of a hypodermic syringe. Injection of a patient with radioactive material by means of a hypodermic syringe has been found to present serious health hazards to the person preparing and administering the injection. This is due to radioactivity emanating from the radioactive material which is to be injected.

As a result of the health hazards presented, it has been proposed to shield both the vial, containing the radioactive material and the hypodermic syringe which is to be loaded, with material, such as lead and lead glass, which is substantially impervious to the passage of radioactive emissions. As a rule, this has been accomplished with respect to the vial, by placing the vial in a snug-fitting sheath of lead which extends to the shoulders of the vial. The hypodermic syringe is shielded, generally, by a lead-glass shield which surrounds the barrel of the hypodermic syringe.

The shielding of the dose vial and hypodermic syringe, as described, although affording some protection to the person loading and discharging the loaded hypodermic syringe does not provide adequate protection during the loading operation. Consequently, during the loading operation, the technician or operator is subjected to an undesirable amount of radiation.

The present invention is a shielding assembly which affords greater protection to the person loading a hypodermic syringe with radioactive material and in addition provides advantages previously described.

In my copending U.S. patent application Ser. No. 587,179, filed June 16, 1975, now U.S. Pat. No. 3,993,063, a protective shielding assembly is disclosed which comprised an inner sleeve, an intermediate sleeve and an outer protective sleeve connected to the inner sleeve. The present invention is directed to a protective shielding assembly comprising an inner sleeve assembly and an outer guiding sleeve assembly which axially extends to cover the shoulders and cap of the vial as more fully described hereinafter.

Further advantages of the present invention are readily apparent from the following description and from the accompanying drawings wherein.

Figure 1:
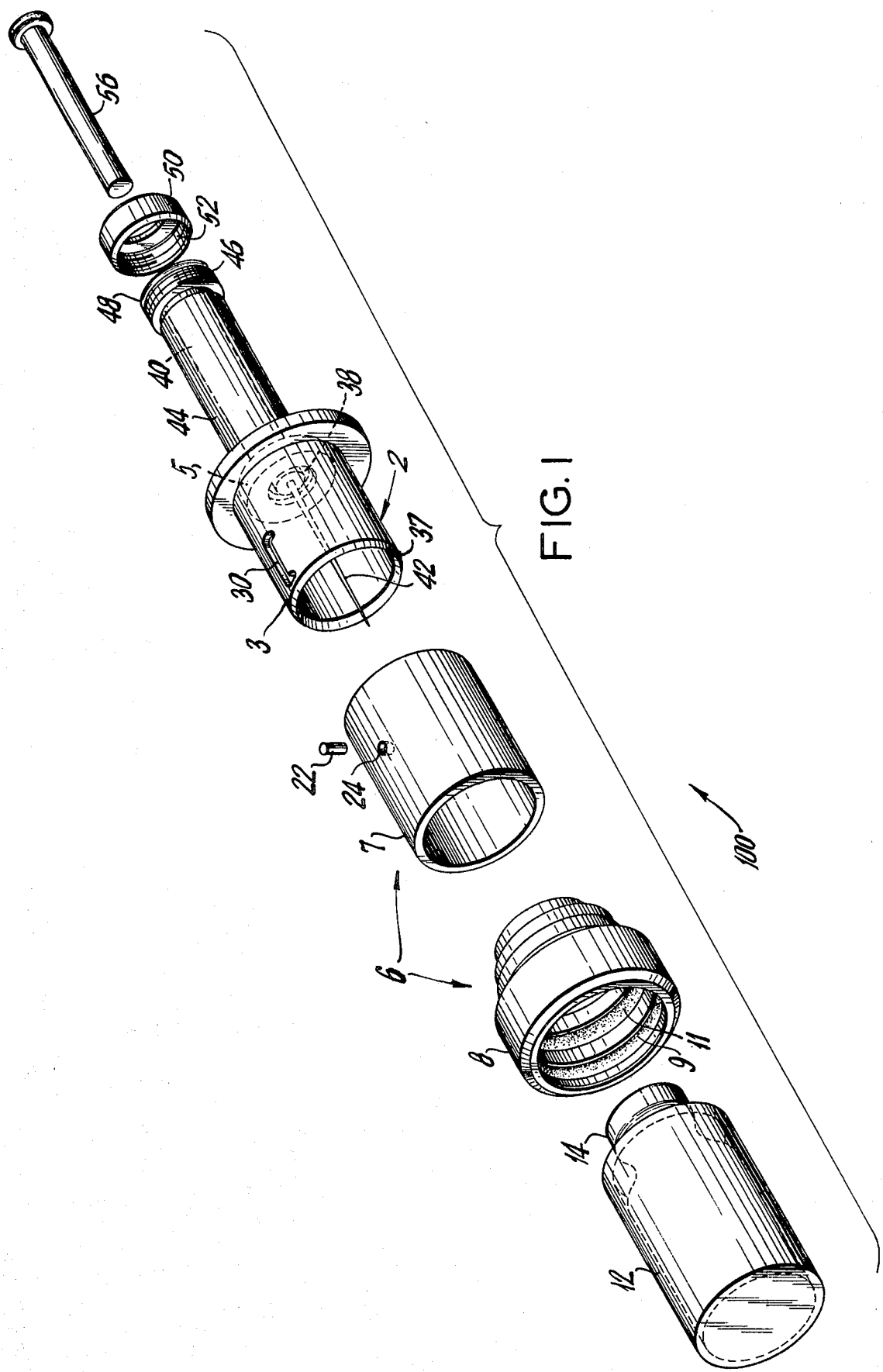
FIG. 1 is an exploded perspective view of the shielding assembly of this invention in conjunction with a dose vial and a hypodermic syringe.
Figure 2:
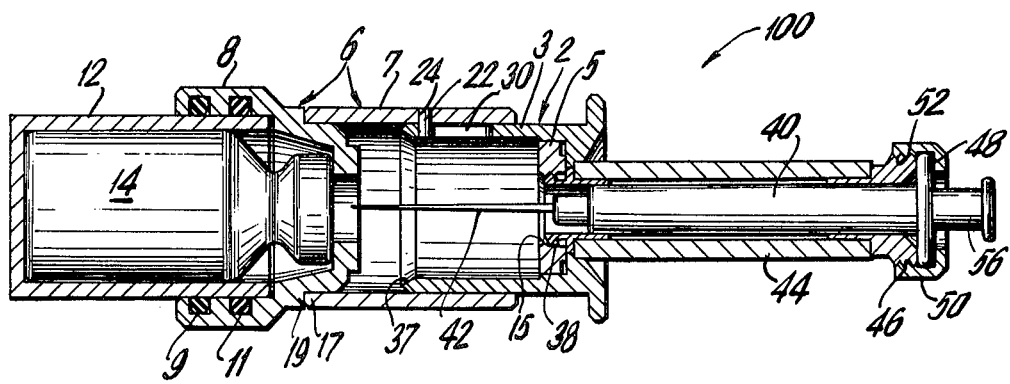
FIG. 2 is a longitudinal section of the shielding assembly connected to the dose vial and hypodermic syringe, prior to penetration of the dose vial.
Figure 3:
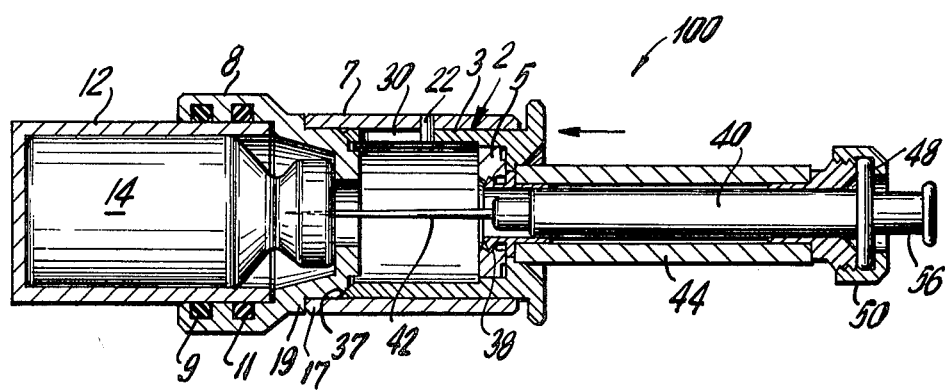
FIG. 3 is a longitudinal section, similar to FIG. 2, showing the shielding assembly in a vial puncturing position.
Figure 4:
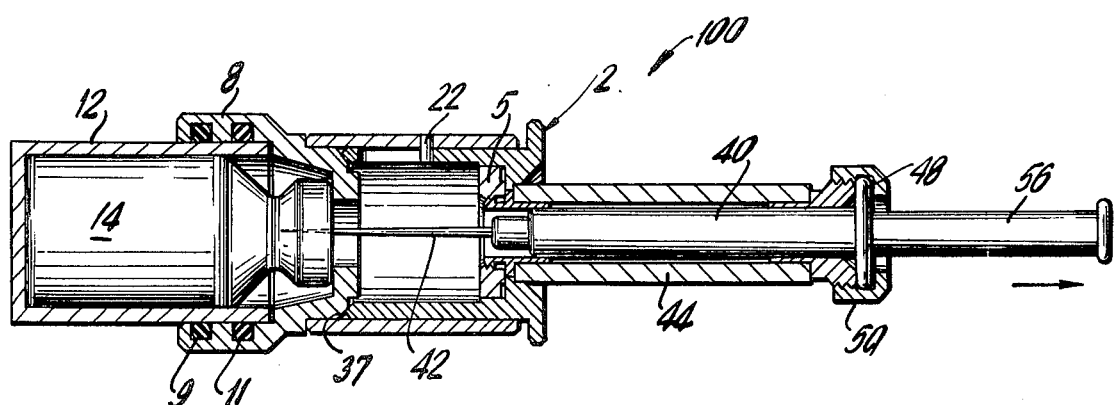
FIG. 4 is a longitudinal section, similar to FIGS. 2 and 3, showing the plunger of the hypodermic syringe withdrawn, loading the barrel of the syringe.

Referring now to the accompanying drawings, the protective shielding assembly of this invention designated in general by numeral 100 comprises two main functional members, those being an inner, slidable needle alignment sleeve assembly 2 and an outer, cap-like, protective shield assembly 6 which slides in conjunction with inner sleeve assembly 2, the two members, when assembled, being in contact as shown in FIGS. 2, 3 and 4. Inner sleeve assembly 2 as shown in FIG. 1 is illustrated in the drawings as comprising coaxially aligned sleeve section 3 and threaded section 5 which is adhesively attached to sleeve section 3, as will be subsequently discussed. Outer sleeve assembly 6 as shown in FIG. 1 is illustrated in the drawings as comprising coaxially aligned guiding sleeve section 7 and shielding shroud section 8 which is adhesively attached to sleeve section 7, as will be subsequently discussed.

The protective shielding assembly of this invention is adapted for the loading of a hypodermic syringe, the parts of which are identified in the drawings as: needle 42, syringe barrel 40, and syringe plunger 56, with the contents from a standard vial designated by numeral 14.

In the embodiment shown in the drawings, inner, slidable, needle alignment sleeve assembly 2 has a longitudinal slot 30 in sleeve section 3 and a rear threaded section 5 for receiving complementary threaded section 38 which is adhesively attached to syringe shield 44, as will be subsequently discussed. Needle alignment sleeve assembly 2 fits snugly within but in slidable relationship to outer sleeve assembly 6 with longitudinal slot 30 of sleeve section 3 aligned with hole 24 of outer sleeve section 7. Once sleeve assembly 2 is placed within outer sleeve assembly 6 and aligned, as described, pin 22 is pressed flush into hole 24 and extends into longitudinal slot 30 of needle alignment sleeve section 3. Pressed pin 22 rides in longitudinal slot 30 and limits the degree of forward and rearward movement of needle alignment sleeve assembly 2 relative to outer sleeve assembly 6, as shown in FIGS. 2, 3 and 4.

The actual length of needle alignment sleeve section 3 and longitudinal slot 30 therein are such as to allow for complete penetration of vial 14, to a desired depth, by needle 42 of the hypodermic syringe as shown in FIGS. 3 and 4 of the drawings.

Guiding sleeve section 7 and shielding shroud section 8 are joined together adhesively, by press-fit or the like, to form the unitary outer sleeve assembly 6. One end of shielding shroud section 8 axially extends into the end of guiding sleeve section 7 situated furthest from the hypodermic syringe. The other end of shielding shroud section 8 extends axially toward vial shield 12 overlapping and enclosing the shoulders of vial shield 12 at all times when the protective shielding assembly of this invention is assembled. Outer sleeve assembly 6 is secured to vial shield 12 by means of a compression fit of elastomeric O-rings 9 and 11 situated within the end of shielding shroud section 8 enclosing the shoulders of vial shield 12. Although a multiplicity of O-rings may be employed, at least one O-ring should be employed.

Threaded section 5 of needle alignment sleeve assembly 2 is coaxially secured within inner sleeve section 3 at the end thereof facing the hypodermic syringe. Sleeve section 3 and threaded section 5 may be joined together adhesively, by press-fit or the like to form the unitary needle alignment sleeve assembly 2. Threaded section 5 has a bore extending axially therethrough and coaxially aligned with sleeve section 3, inner diameter walls of threaded section 5 having threads 15 adapted to receive a complementary threaded member.

The protective shielding assembly, with its two members 2 and 6 assembled and coaxially mounted is ready to receive and securely hold syringe sheath 44, through which the hypodermic syringe is to be slidably inserted. In the embodiment shown in the accompanying drawings, this is accomplished by providing syringe sheath 44 with a threaded member 38 which threads into complementary threads 15 of threaded section 5 of needle alignment sleeve assembly 2. Consequently, syringe sheath 44 is simply screw threaded into the protective shielding assembly. The size and configuration of threaded sections 38 and 5 are such as to accurately align needle 42 of the hypodermic syringe with the center of the septum of vial 14, as shown in FIGS. 2, 3 and 4.

Threaded members or fittings 38 and 5 are conveniently attached to syringe shield 44 and inner sleeve section 3, respectively, by use of a suitable bonding agent such as an epoxy resin. A detailed description of suitable epoxy resin compositions appears in U.S. Pat. No. 3,788,321 to Thomas D. Reitler.

Syringe sheath 44 is also provided, at its end opposite threaded member 38, with threaded member or fitting 46. Threaded member 46 in conjunction with cap-nut 50, having threads 52, locks flange 48 of the hypodermic syringe within syringe sheath 44, once the hypodermic syringe is inserted into syringe sheath 44 to a position shown in FIG. 2.

The entire assembly is then connected to vial 14.

This is conveniently accomplished, as shown in the drawings, by sliding the end of shielding shroud section 8 containing O-rings 9 and 11 therewithin over vial shield 12 which surrounds vial 14. The friction force of O-rings 9 and 11 within shielding shroud 8 secures outer sleeve member 6 to vial shield 12. The internal annular shoulder of sleeve section 7 abuts an annular ridge 19 extending around the outer periphery of shielding shroud section 8 at the end thereof opposite the end containing O-rings 9 and 11 therewithin. A close fit is formed between ridge 19 and shoulder 17.

FIG. 2 of the accompanying drawings shows the protective shielding assembly, providing complete shielding protection, connected to vial 14 with the hypodermic syringes in position ready for use.

On applying force to the protective shield assembly in the direction of vial 14, the hypodermic syringe, and needle alignment sleeve assembly 2 of the protective shielding assembly moves toward vial 14 resulting in syringe needle 42 puncturing the septum of vial 14 and penetrating vial 14 as shown in FIG. 3. The depth of penetration of syringe needle 42 in vial 14 is controlled by the length of longitudinal slot 30 in needle alignment sleeve assembly 2. Penetration of syringe needle 42 into vial 14 is stopped when pressed pin 22 abuts the inner wall of needle alignment slot 30 in sleeve assembly 2 and the annular shoulders 37 of needle alignment sleeve assembly 2 abut a portion of the front face of vial 12 as shown in FIG. 3.

Loading of the hypodermic syringe is carried out by withdrawing plunger 56 of the hypodermic syringe as shown in FIG. 4.

The loaded hypodermic needle is then returned to the position shown in FIG. 2 by simply retracting the hypodermic needle from vial 14.

Removal of the loaded hypodermic syringe from the protective shielding assembly of this invention is effected by unscrewing syringe sheath 44 from the protective shielding assembly. The loaded hypodermic syringe can then be used in an injection operation.

After the injection operation, the hypodermic syringe can be removed from the syringe sheath by unscrewing cap-nut 50 from threaded member 46.

The protective shielding assembly of this invention can be used with standard glass vials and hypodermic needles. The glass vials generally have rubber septums held in place by a crimped aluminum cap. The shield which surrounds the glass vial can be of any material which is substantially impervious to the passage of radioactive emissions although lead is preferred.

Although the present invention has been exemplified in reference to an O-ring looking mechanism between the vial shield 12 and shroud section 8, it is to be understood that mechanical clamping such as a machine tool collet can be used to secure shroud section 8 to vial shield 12.

Outer sleeve section 7 and sleeve section 5 can be of any suitable material which is substantially impervious to the passage of radioactive emissions, particularly gamma rays, i.e., it will supply moderate radiation absorption. The material for outer sleeve section 7 also has sufficient rigidity to support pin 22. Suitable materials include tungsten alloys, tantalum, stainless steel and the like. A preferred material for sleeve 6 is stainless steel. Inner sleeve section 3 and shielding shroud section 8 can be made of a lead alloy containing at least 85 percent lead by weight, preferably an antimony lead alloy at least 85 percent lead by weight.

The shield 44 surrounding the barrel 40 of the hypodermic syringe is generally made of lead-glass to allow observation of the amount of material in barrel of the hypodermic syringe. Threaded members 38 and 46 which are adhesively attached to shield 44 are usually metal but can be plastic, if so desired, as can be the locking assembly for flange 48.

Also, if desired, a protective cap can be mounted over locking nut 50 to provide a shield around the plunger area when the plunger is withdrawn as shown in FIG. 4.

It is to be understood that whenever lead is indicated to be used lead alloys can be substituted.

Outer sleeve 2 will cover slot 30 at all times without leaving an uninterrupted path for radiation. Also, shielding shroud section 8 provides an internal barrier to radiation from the vial 14 when the hypodermic syringe is withdrawn from the shielding assembly as shown in FIG. 4.

What is claimed is:

1. A protective shielding assembly, adapted to protect a user from exposure to radiation emitted by a radioactive material, suitable for use in the loading of a hypodermic syringe with said radioactive material, said assembly adapted at one end to be connected to a first protective shield surrounding a vial having a cap and shoulders and at its opposite end adapted to be connected to a second protective shield, surrounding the barrel of said hypodermic syring at the needle end thereof and fixedly holding said hypodermic syringe, said assembly comprising an outer sleeve connectable to said first protective shield and protecting said cap and shoulders of said vial when connected to said first protective shield, an inner protective sleeve connectable to said second protective shield and connected to said outer sleeve, said inner sleeve being in contact with and slidable with respect to said outer sleeve, said inner and outer slidable sleeves being capable of moving said second protective shield toward said vial causing penetration thereof by said needle of said hypodermic syringe, wherein said inner sleeve and at least the portion of said outer sleeve protecting said cap and shoulders of said vial are made of a material comprising lead alloy containing at least 85 percent lead by weight.

2. A protective shielding assembly as defined in claim 1 further including elastomeric O-ring sealing means concentrically mounted within one end of said outer sleeve for connecting said outer sleeve to said first protective shield.

3. A protective shielding assembly, adapted to protect a user from exposure to radiation emitted by a radioactive material, suitable for use in the loading of a hypodermic syringe with said radioactive material, said assembly adapted at one end to be connected to a first protective shield assembly surrounding a vial having a cap and shoulders and at its opposite end adapted to be connected to a second hypodermic syringe at the needle end thereof and fixedly holding said hypodermic syringe, said assembly comprising as concentrically mounted members, an outer sleeve connectable to said first protective shield and having a protective axial extension overlapping said first protective shield and protecting said cap and shoulders of said vial when connected to said first protective shield, an inner protective sleeve connectable to said second protective shield, said outer sleeve and said inner sleeve in contact with and slidably movable with respect to one another, said inner sleeve on being moved toward the vial effecting movement of said second protective shield toward said vial causing penetration thereof by said needle of said hypodermic syringe, wherein said inner sleeve and at least said protective axial extension of said outer sleeve are made of a material comprising a lead alloy containing at least 85 percent lead by weight.

4. A protective shielding assembly as defined in claim 3 further including elastomeric O-ring sealing means concentrically mounted with one end of said outer sleeve for connecting said protective axial extension of said outer sleeve to said first protective shield.

5. A protective shielding assembly, adapted to protect a user from exposure to radiation emitted by a radioactive material, suitable for use in the loading of a hypodermic syringe with said radioactive material, said assembly adapted at one end to be connected to a first protective shield surrounding a vial having a cap and shoulders and at its opposite end adapted to be connected to a second protective shield, surrounding the barrel of said hypodermic syringe at the needle end thereof and fixedly holding said hypodermic syringe, said assembly comprising an inner protective sleeve having a longitudinal slot therein and mounted within an outer sleeve, said outer sleeve having a pin extending through the wall thereof and riding in the slot of said inner sleeve, said pin limiting the degree of slidable movement of said inner sleeve, said outer sleeve having a protective axial extension overlapping said first protective shield and protecting said cap and shoulders of said vial when said outer sleeve is connected to said first protective shield, said outer sleeve slidably mounted on said inner protective sleeve and connected thereto, said inner and outer slidable sleeves being capable of moving said second protective shield toward said vial causing penetration thereof by the needle of the hypodermic syringe, wherein said inner sleeve and at least said protective axial extension of said outer sleeve are made of a material comprising a lead alloy containing at least 85 percent lead by weight.

6. A protective shielding assembly as defined in claim 5 further including elastomeric O-ring sealing means concentrically mounted within one end of said outer sleeve for connecting said protective axial extension of said outer sleeve to said first protective shield.

* * * * *

UNITED STATES PATENT OFFICE
CERTIFICATE OF CORRECTION

Patent No. 4,092,546      Dated May 30, 1978

Inventor(s) Edward W. Larrabee

It is certified that error appears in the above-identified patent and that said Letters Patent are hereby corrected as shown below:

In claim 3, column 5, line 33 reading: "connected to a second hypodermic syringe at the needle" should read-- connected to a second protective shield surrounding the barrel of a hypodermic syringe at the needle--.

Signed and Sealed this

Twentieth Day of February 1979

[SEAL]

Attest:

RUTH C. MASON
Attesting Officer

DONALD W. BANNER
Commissioner of Patents and Trademarks